United States Patent [19]

Itzel et al.

[11] Patent Number: 4,892,866

[45] Date of Patent: Jan. 9, 1990

[54] STABILIZED PESTICIDAL COMPOSITION

[75] Inventors: Hanshelmut Itzel, Gau-Algesheim; Manfred Dewenter, Badenheim; Siegfried Henke, Welgesheim, all of Fed. Rep. of Germany

[73] Assignee: Shell Internationale Research Maatsshappij B. V., The Hague, Netherlands

[21] Appl. No.: 223,078

[22] Filed: Jul. 22, 1988

[30] Foreign Application Priority Data

Aug. 7, 1987 [DE] Fed. Rep. of Germany ....... 3726339

[51] Int. Cl.⁴ .............................................. A01N 57/00
[52] U.S. Cl. ..................................... 514/119; 514/970; 514/971
[58] Field of Search ......................... 514/119, 970, 971

[56] References Cited

U.S. PATENT DOCUMENTS 2,996,531  8/1961  Young ................................. 558/107
3,090,719  5/1963  Pinemonti et al. ................... 514/119

FOREIGN PATENT DOCUMENTS 237004  10/1985  Japan .
791824   3/1958  United Kingdom .
903159   8/1962  United Kingdom .

Primary Examiner—Allen J. Robinson

[57] ABSTRACT

The invention provides a pesticidal composition comprising, as active ingredient, dimethoate together with at least one inert carrier therefor, characterized in that the composition contains, as stabilizer, a cyclopropene fatty acid or an oil containing at least 1% w of a cyclopropene fatty acid.

4 Claims, No Drawings

STABILIZED PESTICIDAL COMPOSITION

The invention relates to stabilised pesticidal compositions, and more particularly to the stabilisation of pesticidal compositions containing dimethoate.

Dimethoate, O,O-dimethyl-S-methylcarbamoylmethyl phosphorodithioate, is a well-known and widely used systemic and contact insecticide. It is described, together with methods for its preparation, for example in UK Patent No. 791,824 and U.S. Pat. No. 2,996,531. One problem of dimethoate is that it is thermally unstable and at temperatures of about 50° C. or more it can be subject to uncontrolled thermal breakdown, resulting in explosions. This is clearly a greater potential drawback in hot climates, and particularly in developing countries where storage facilities do not enable products to be protected from the sun's rays and where products are liable to be transported in open trucks and stored temporarily in the open.

In such conditions unprotected storage, or storage for very long periods of time can easily result in products being unusable giving rise to problems of disposal, and in some cases fires have been caused by auto-ignition of stored products.

It has now surprisingly been found that when dimethoate is stored in admixture with an oil containing a cyclopropene fatty acid significantly reduced thermal degradation can be observed.

Accordingly the present invention provides a pesticidal composition comprising, as active ingredient, dimethoate together with at least one inert carrier therefor, characterised in that the composition contains, as stabiliser, a cyclopropene fatty acid or an oil containing at least 1% w of a cyclopropene fatty acid.

Typical examples of cyclopropene fatty acids are malvalic acid (2-octyl-1-cylopropene-1-heptanoic acid) (otherwise also known as malvic acid or halphen acid) and sterculic acid (2-octyl-1-cyclopropene-1-octanoic acid) (also known as sterculinic acid). Oils containing these acids can be extracted from seeds of the kapok tree (*Cieba pentandra*) (viz. kapok seed oil) and from *Sterculia* species, particularly *Sterculia foetida*. These acids are also to be found in other plants, e.g. durian (*Durio zibethinus*), gnemon (*Gretum gnemon*) and in species of the *Malvaceae* family.

Preferably the stabiliser in a composition of the invention comprises malvalic or sterculic acid or oil from seeds of the kapok tree or from *Sterculia* species. The stabiliser may very conveniently be kapok seed oil.

It is preferred for the weight ratio of cyclopropene fatty acid(s): dimethoate in a composition of the invention to be in the range 0.1:1 to 1.5:1, more preferably 0.4:1 to 1:1, advantageously 0.5:1 to 0.7:1.

When the stabiliser in a composition of the invention is kapok seed oil, the weight ratio kapok seed oil: dimethoate is preferably in the range 1:1 to 10:1, more preferably 4:1 to 6:1.

The invention also provides a method of stabilising a pesticidal composition comprising, as active ingredient, dimethoate together with at least one inert carrier therefor, the method comprising incorporating in the composition, as stabiliser, a cyclopropene fatty acid or an oil containing at least 1% w of a cyclopropene fatty acid.

Preferred methods of the invention employ the same stabilisers and weight ratios as indicated above in relation to compositions of the invention.

Pesticidal compositions comprise at least one active ingredient together with at least one inert carrier therefore, preferably at least two carriers, at least one of which is a surface-active agent.

A carrier may be a solid or liquid material, which may be inorganic or organic and of synthetic or natural origin. Typical solid carriers include natural and synthetic clays and silicates, for example natural silicas, for example diatomaceous earths, and aluminium silicates, for example kaolinites, montmorillonites and micas. Typical liquid carriers are ketones, for example methylnaphthalenes, petroleum fractions, for example petroleum xylenes and light mineral oils, and chlorinated hydrocarbons, for example carbon tetrachloride. Mixtures of liquids are often suitable.

One or more surface-active agents and/or stickers can be included in a pesticidal composition. A surface-active agent may be an emulsifying agent or a dispersing agent or a wetting agent; it may be non-ionic or ionic. Any of the surface-active agents usually applied in formulating insecticides may be used. Examples of suitable surface-active agents are the sodium and calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol, condensates of these with ethylene oxide and/or propylene oxide; condensation products of fatty alcohols or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates, such as sodium dodecylbenzene sulphonate; and polymers of ethylene oxide and copolymers of ethylene oxide and propylene oxide.

A pesticidal composition may for example be formulated as a wettable powder, microcapsules, a dust, granules, a solution, an emulsifiable concentrate, an emulsion, a suspension concentrate or an aerosol. Compositions may have controlled release properties, or may be suitable for use as a bait.

Wettable powders usually contain 25, 50 or 75% w of active ingredient and may contain, in addition to inert solid material, 3–10% w of a dispersing agent and, where necessary, 0–10% w of a stabiliser, a penetrant and/or a sticker. A dust is usually formulated as a dust concentrate having a composition similar to that of a wettable powder but without a dispersant, and is diluted in the field with further solid carrier to give a composition usually containing ½–10% w of active ingredient.

Granules usually have a size in the range of from 10 to 100 BS mesh (1.676–0.152 mm) and may be manufactured by agglomeration or impregnation techniques. Generally, granules will contain ½–25% w active ingredient and 0–10% w of additives, for example a stabiliser, slow release modifier and/or a binding agent.

Emulsifiable concentrates usually contain, in addition to a solvent, and, when necessary, co-solvent, 10–50% w/v active ingredient, 2–20% w/v emulsifier and 0–20% w/v of other additives, for example a stabiliser, a penetrant and/or a corrosion inhibitor. A suspension concentrate is a stable, non-sedimenting, flowable product and usually contains 10–75% w active ingredient, 0.5–15% w of dispersing agent, 0.1–10% w of suspending agent, for example protective colloid and/or a thioxotropic agent, and 0–10% w of other additives including, for example, a defoamer, a corrosion inhibitor, a stabiliser, a penetrant and/or a sticker, and as dispersant, water or an organic liquid in which the active ingredient is substantially insoluble; certain organic additives and/or inorganic salts may be dissolved in the dispersant to assist in preventing sedimentation or as anti-freeze for water.

The aqueous dispersions and emulsions formed by diluting a wettable powder or an emulsifiable concentrate are themselves pesticidal compositions. Such dispersions and emulsions may be of the water-in-oil or of the oil-in-water type, and may have a thick "mayonnaise"-like consistency.

Pesticidal compositions may also contain other ingredients, for example, one or more other compounds possessing pesticidal, herbicidal or fungicidal properties, or attractants, for example pheromones or food ingredients, for use in baits and trap formulations.

The invention also includes a method of combating pests at a locus which comprises applying to that locus a pesticidal composition according to the invention. The invention will be further understood from the following illustrative Examples.

EXAMPLE 1

A formulation of dimethoate was prepared by admixing components according to the following composition.

| I | % w/w |
|---|---|
| Dimethoate | 11 |
| Cyclohexanone | 34 |
| Kapok seed oil | 55 |
| (equivalent to 6–7% w/w cyclopropene fatty acids) | |

For comparison purposes storage stability of formula I was monitored together with that of comparative formulation A, which consisted of 55.4% w/w dimethoate and 44.6% w/w cyclohexanone, over a range of temperatures for up to 36 months. Results are given in Table I following:

TABLE I

| | % breakdown of dimethoate | | | | | | | |
|---|---|---|---|---|---|---|---|---|
| Temperature | 20° C. (ambient) | | 37° C. | | 50° C. | | 60° C. | |
| Formulation | I | A | I | A | I | A | I | A |
| Period (months) | | | | | | | | |
| 1 | | | 0 | 1 | 0 | 80 | 11 | * |
| 6 | | | 0 | 10 | | | | |
| 12 | | | 0 | 40 | | | | |
| 24 | 0 | 10 | 0 | 70 | | | | |
| 36 | 0 | 40 | 0 | 100 | | | | |

*strongly exothermic breakdown

The results given in Table I show the very much greater thermal stability conferred upon a formulation of dimethoate and cyclohexanone by the inclusion of an oil (kapok oil) containing cyclopropene fatty acids.

We claim:

1. A pesticidal composition comprising, as active ingredient, a pesticidally effective amount of dimethoate together with at least one inert carrier therefor, characterized in that the composition contains a stabilizing effective amount of a stabilizer comprising a cyclopropene fatty acid, said stabilizer being selected from the group consisting of malvalic acid, sterculic acid, and oil from seeds of the kapok tree, from *Sterculia* species, from *Durio zibethinus*, from *Gretum gnemon* or from species of the *Malvaceae* family.

2. A composition according to claim 1 wherein the stabilizer is selected from the group consisting of malvalic acid, sterculic acid and oil from seeds of the kapok tree or from *Sterculia* species.

3. A composition according to claim 1 wherein the weight ratio of cyclopropene fatty acid:dimethoate is in the range of 0.1:1 to 1.5:1.

4. A composition according to claim 1, 2 or 3 wherein the stabilizer comprises oil from seeds of the kapok tree, the weight ratio of said oil:dimethoate being in the range of 1:1 to 10:1.

* * * * *